United States Patent
Ostreicher (12)

(10) Patent No.: US 6,415,955 B1
(45) Date of Patent: Jul. 9, 2002

(54) PLASTER EJECTOR GUN WITH DISPOSABLE CARTRIDGE

(76) Inventor: David Ostreicher, 93 Division St., Levittown, NY (US) 11756

( * ) Notice: Subject to any disclaimer, the term of this patent is extended or adjusted under 35 U.S.C. 154(b) by 0 days.

(21) Appl. No.: 09/812,458

(22) Filed: Mar. 20, 2001

(51) Int. Cl.[7] ............................................. B65D 35/22
(52) U.S. Cl. ........................ 222/94; 222/95; 222/326; 206/222
(58) Field of Search ....................... 222/94, 95, 105, 222/326, 391; 206/219, 222

(56) References Cited

U.S. PATENT DOCUMENTS

| | | | |
|---|---|---|---|
| 3,596,801 A | * 8/1971 | Barnsck | 206/222 |
| 3,730,394 A | * 5/1973 | Woodson | 222/326 |
| 4,081,256 A | 3/1978 | Donnelly | |
| 4,212,840 A | 7/1980 | Cliff et al. | |
| 4,386,717 A | * 6/1983 | Koob | 222/94 |
| 4,842,165 A | 6/1989 | Van Coney | |
| 4,863,072 A | 9/1989 | Perler | |
| 5,304,239 A | 4/1994 | Schwabe | |
| 5,489,207 A | 2/1996 | Dragan et al. | |
| 5,624,260 A | 4/1997 | Wilcox et al. | |
| 5,860,739 A | 1/1999 | Cannon | |

OTHER PUBLICATIONS

US 5,297,689, 03/1994, Martin (withdrawn).

* cited by examiner

*Primary Examiner*—Philippe Derakshani
(74) *Attorney, Agent, or Firm*—Michael I. Kroll (57) ABSTRACT

The present invention 10 discloses an apparatus for extruding plaster including a plaster pump gun 34 and disposable containers 24 for use therein. The containers 24 consist of a plastic bag-like container 24 having a predetermined amount of plaster powder 26 contained therein and a second burstable container of water 28 also contained therein. An alternative bag-like container 24 is also disclosed having a first plaster containing chamber 26 and a second water containing chamber 50 therein separated by a thin, weak membrane or seal 48 which may be easily ruptured. In use, the bag-like container 24 is compressed thereby bursting the water container 28 or membrane 48 which wets the plaster powder 26 which is thereafter kneaded until the desired consistency has been reached. Thereafter, the distal end 36 of the container 24 is compressed forming a nozzle-like end. The nozzle-like end of the container 24 is thereafter placed into the outlet nozzle 20 of the ejector gun 34 and the container 24 is placed in the bore 18 of the gun 34. The ejector gun trigger 16 is then depressed so that the ejector gun piston plate 46 compresses the plaster tube mixture in the container 24, forcing a small plaster mixture out tip 38 out of the ejector gun nozzle 20 which tip is then cut-off. After the plaster has been expelled from the ejector gun nozzle 20, the nozzle 20 is removed and the container 24 is removed and disposed. Because the container 24 covers all interior surfaces of the ejector gun 34, there is no clean up necessary for the ejector gun.

22 Claims, 8 Drawing Sheets

PLASTER EJECTOR GUN WITH DISPOSABLE CARTRIDGE

BACKGROUND OF THE INVENTION

1. Field of the Invention

The present invention relates generally to an improved apparatus and method for extruding plaster, and more specifically to a device for dispensing a plaster preparation, including dispensing apparatus and disposable cartridges. The cartridges consist of a plastic bag-like container, having a predetermined amount of plaster powder enclosed therein. Also, within the container is a second burstable container having a measured amount of water therein.

At the time of use the bag-like container is compressed bursting the water container. The package is kneaded until the desired consistency has been reached. One distal end is compressed forming a cylindrical nozzle-like end.

The ejector gun is comprised of a cylindrical container having a removable nozzle at one distal end and a piston at the other. The cylindrical container also has a handle with a trigger connected to the piston for advancing the piston compressing the plaster paste toward the ejector nozzle.

The plaster paste container is inserted into the injector gun by removing the ejector gun nozzle and inserting the plaster tube or container therein. The plate tube soft nozzle-like end is positioned within the ejector gun nozzle as the ejector gun nozzle is attached to the ejector gun.

As the ejector gun trigger is depressed the ejector gun piston compresses the plaster tube mixture. The ejector gun piston increases the pressure until the soft nozzle is slightly extruded from the ejector gun nozzle. The extruded portion extending from the ejector nozzle is clipped whereby the contents of the bag can be expelled using the ejector gun handle. Once the plaster has been expelled from the soft container the ejector gun nozzle is removed and the empty soft container is disposed. Because the soft package covers all interior surfaces of the ejector gun there is no cleanup of the ejector gun.

2. Description of the Prior Art

There are other apparatus for designed for dispersing plaster. Typical of these is U.S. Pat. No. 4,081,256 issued to Donnelly on Mar. 28, 1978.

Another patent was issued to Cliff et al. on Jul. 15, 1980 as U.S. Pat. No. 4,212,840. Yet another U.S. Pat. No. 4,842,165 was issued to Van Coney on Jun. 27, 1989 and still yet another was issued on Sep. 5, 1989 to Perler as U.S. Pat. No. 4,863,072.

Another patent was issued to Martin on Mar. 29, 1994 as U.S. Pat. No. 5,297,698. Yet another U.S. Pat. No. 5,304,239 was issued to Schwa et al., on Apr. 19, 1994. Another was issued to Dragan on Feb. 6, 1996 as U.S. Pat. No. 5,489,207 and another was issued on Apr. 29, 1997 to Wilcox et al., as U.S. Pat. No. 5,624,260, and still yet another was to Cannon on Jan. 19, 1999 to as U.S. Pat. No. 5,860,739.

U.S. Pat. No. 4,081,256

Inventor: William R. Donnelly

Issued: Mar. 28, 1978

A particulate composition producing an endothermic reaction when mixed with water, and a cold pack containing such a composition, and water isolated therefrom until the intended time of use. The composition consists essentially of, in parts by weight, about 65 to about 130 parts urea, about 35 to about 80 parts hydrated sodium acetate (Na $C_2H_3O_2 \cdot 3H_2O$), about 18 to about 40 parts potassium chloride, potassium nitrate, or mixtures thereof, about 18 to about 30 parts ammonium chloride, and about 6 to about 10 parts quar gum. A cold pack comprises an outer sealed, flexible, impermeable enclosure containing the composition, and an inner sealed, flexible, impermeable, easily ruptured enclosure containing about 85 to about 140 parts by weight water. The pack reaches and maintains a temperature of about −7.degree. C. for up to 30 minutes, and is moldable to conform to the surfaces being cooled.

U.S. Pat. No. 4,212,940

Inventor: George S. Cliff, et al.

Issued: Jul. 15, 1980

This invention concerns an improved apparatus for extruding abrasive pastes, especially those which contain ground glass together with polymerizable material, and which comprises a conventional piston and cylinder extrusion apparatus in which the working surfaces are protected by a replaceable lining system consisting of a thin tubular liner and two discs substantially closing its ends and enclosing the paste to be extruded. In the preferred embodiment (FIG. 1) the lining system is made of polypropylene.

U.S. Pat. No. 4,842,165

Inventor: Robert H. Van Coney

Issued: Jun. 27, 1989

A resilient squeeze bottle-dispensing package capable of dispensing viscous products without excessive air entrainment and belching on successive dispensing cycles. In a preferred embodiment, the viscous product is preferably suspended inside a resilient squeeze bottle in a thin flexible bag. The flexible bag is secured about its perimeter to the interior of the squeeze bottle at its top and approximately at its midpoint to facilitate both complete emptying of product and desirable suckback characteristics when the opposed squeezing forces are removed from the resilient outer wall of the bottle. A suckback valve is located between the dispensing orifice in the shroud of the package and the flexible bag to limit the amount of air which can enter the package through the dispensing orifice at the conclusion of each dispensing cycle and to prevent slumping of viscous product remaining in the shroud into the bottom of the flexible bag between dispensing cycles. An air check valve is preferably provided in the bottom of the resilient squeeze bottle to facilitate a pressure buildup within the bottle when opposed squeezing forces are applied thereto.

U.S. Pat. No. 4,863,072

Inventor: Robert Perler

Issued: Sep. 5, 1989

Apparatus for the delivery of light-curable composite dental filling material comprises a tubular composite reservoir, plunger and slider. The slider is free to move longitudinally along the reservoir but is matingly mounted to facets on the outside surface of the reservoir to prevent angular movement of the slider relative to the reservoir. The plunger consists of a shaft threaded to mate with the threaded inside diameter of the composite reservoir. The plunger also has a disk integrally formed to end of the shaft at one end and a male front piece at the other. The male front piece mates with a female fitting of a separate composite extrusion element.

U.S. Pat. No. 5,297,698

Inventor: Thomas W. Martin

Issued: Mar. 29, 1994

An assembly for mixing and dispensing preparations such as dental cements includes a capsule and a lever actuated dispensing device. The capsule is received in a first orientation of the dispensing device for initial movement of a piston of the capsule to combine two components in a mixing chamber of the capsule. The capsule is received in a second orientation when dispensing of the components is desired. The capsule includes flanges engageable with one or more retention members of the dispensing device, and the flanges are positioned to substantially utilize the mechanical advantage provided by the dispensing device regardless of whether the capsule is in the first orientation or in the second orientation. The flanges are also arranged to substantially prohibit bursting of the capsule when the components are discharged from the mixing chamber, and essentially preclude dispensing of the components when the capsule is in the first orientation.

U.S. Pat. No. 5,304,293

Inventor: Peter Schwabe et al.

Issued: Apr. 19, 1994

In the preparation of a dental appliance wherein an investment compound is mixed with a liquid and then cast, the improvement wherein the investment compound is a plaster- or phosphate-bound investment compound which is free of an anionic surface-active agent and containing an iso-paraffin of the formula ##STR1## in which n denotes 2, 3, 4 or 5.

U.S. Pat. No. 5,489,207

Inventor: William B. Dragan

Issued: Feb. 6, 1996

A manual dental extruder or syringe gun having a front end with rigid side walls and an opening therein adapted to receive a dental cartridge, capsule, ampoule or tip having a flange. The body portion of the cartridge has a diameter less than that of the lateral width of the opening in the rigid side walls so that the dental cartridge can easily be dropped therein. At one end of the cartridge opening is a flange retainer. After dropping the dental cartridge in the front end, the cartridge is slid forward into the flange retainer. A portion of the rigid side walls extend over the flange when the dental cartridge is in position to be extruded. The rigid side walls improve the durability and strength of the dental extruder and prevents the dental cartridge from being pushed through the end of the extruder due to the large longitudinal forces required to extrude viscous dental materials.

U.S. Pat. No. 5,624,260

Inventor: Malcolm W. Wilcoz et al.

Issued: Apr. 29, 1997

A cartridge for delivery of aqueous paste dental materials is provided, wherein the cartridge comprises a cartridge body made from an injection moldable material comprising polyolefin polymers. The cartridge body having a Moisture Permeability less than 25 g mil/m.sup.2 day atm. and an Oxygen Permeability greater than 180 cm.sup.3 mil/m.sup.2 day atm. The cartridge body comprises at least one chamber adapted for holding and simultaneously dispensing an aqueous paste dental material. The cartridge has a polymerizable aqueous paste dental material contained within the chamber of the cartridge body, and the cartridge is specially adapted to be mounted in a hand-held ejector-type gun.

U.S. Pat. No. 5,860,739

Inventor: Mark L. Cannon

Issued: Jan. 19, 1999

A dental syringe system including a gun element, for association with a tip element, to mix and dispense respective dental materials of and while the materials yet have plastic or flowable consistency. The gun has a chamber in which to load cartridges of respective such materials, a motor, two plungers, a ram to move relative to the gun, and a trigger-and-gears mechanism to operate the plungers in association with the motor, and separately to operate the ram. The trigger is mounted to move to and between several positions. At one such position, the trigger operates the motor to advance the plungers into respective sites where such cartridges may be loaded and, when cartridges are so loaded, to express materials from the cartridges and the gun. At a subsequent such position, the trigger extends the ran from the gun, and the motor and the plungers disengage. The tip element has a trans-tip passage with a cavity, vanes within the cavity, and a channel from the cavity. When the gun is so loaded and carries the tip element so that the chamber is in communication with the cavity, the trigger is operable in two respects: first, to advance the plungers and to express material from each cartridge into the cavity, and, second, to extend the ram into the cavity, to mix the materials on the vanes, and to urge mixed materials from the tip element via the channel. Two trigger-and-gear mechanisms for the gun are disclosed.

While these dispensing apparatuses may be suitable for the purposes for which they were designed, they would not be as suitable for the purposes of the present invention, as hereinafter described. It is thus desirable to provide a plaster dispensing device that consists of a plaster pump and re-fill cartridges. It is further desirable to provide a cartridge that contains plaster powder separate from a plastic water bag and requires kneading to mix the plaster to its proper consistency.

SUMMARY OF THE PRESENT INVENTION

The present invention discloses an apparatus for extruding plaster including a plaster pump gun and disposable containers for use therein. The plaster containers consist of a plastic bag-like container having a pre-determined amount of plaster powder contained therein and a second burstable container of water also contained therein. An alternative bag-like container is also disclosed having a first plaster containing chamber and a second water containing chamber therein separated by a thin, weak membrane or seal which may be easily ruptured. In use, the bag-like container is compressed thereby bursting the water container or membrane, which wets the plaster powder, which is thereafter kneaded until the desired consistency has been reached. Thereafter, the distal end of the container is compressed forming a nozzle-like end. The nozzle-like end of the container is thereafter placed into the outlet nozzle of the ejector gun and the container is placed in the bore of the gun. The ejector gun trigger is then depressed so that the ejector gun piston plate compresses the plaster tube mixture in the container, forcing a small plaster mixture tip out of the ejector gun nozzle which tip is then cut-off. After the plaster has been expelled from the ejector gun nozzle, the tip nozzle is removed and the container is removed and disposed. Because the container covers all interior surfaces of the ejector gun, there is no clean up necessary for the ejector gun.

A primary object of the present invention is to provide a plaster pump apparatus and disposable cartridge.

Another object of the present invention is to provide a disposable plaster cartridge encapsulating plaster powder, and a burstable water chamber forming an integral part of said plaster cartridge.

Yet another object of the present invention is to provide a disposable plaster cartridge encapsulating measured amounts of plaster powder and water.

Still another object of the present invention is to provide a disposable plaster having a burstable water chamber that can be burst at time of use using normal hand pressure.

Still yet another object of the present invention is to provide a disposable plaster cartridge whereby a measured amount of plaster can be produced as needed by bursting the integral water chamber and kneading the mixture until a desired consistency has been achieved.

Another object of the present invention is to provide a disposable plaster cartridge that can be easily stored until time of use.

Yet another object of the present invention is to provide a disposable plaster cartridge that can be inserted into an ejector gun for controllable dispensing the plaster mixture.

Still another object of the present invention is to provide an ejector gun having a cylindrical bore with a nozzle at one distal end and a piston at the other distal end.

Still yet another object of the present invention is to provide a trigger for controllably advancing the piston toward the nozzle.

Another object of the present invention is to provide an ejector gun having a removable nozzle element providing access to the ejector cylindrical bore.

Additional objects of the present invention will appear as the description proceeds.

The present invention overcomes the shortcomings of the prior art by providing a plaster pump that require no clean up after use, and a disposable no clean up cartridge. Comprising plaster cartridge consisting of a bag-like container encapsulating plaster powder, and a burstable integral water chamber. The bag-like canisters can be easily stored until needed. Whereupon, using hand pressure, the integral water chamber is burst and the plaster water parts are mixed by kneading the bag-like canister until the desired consistency has been achieved. The bag-like canister is inserted into an ejector gun. The trigger is squeezed repeatedly until a portion of the plaster bag extends through the ejector gun nozzle. The bag is cut and its contents are selectively dispensed by squeezing the ejector gun trigger. Once dispensed, the bag is removed from the ejector gun and disposed. Because the interior of the ejector gun never comes into contact with the plaster there is no clean up.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

With regard to reference numerals used, the following numbering is used throughout the drawings.

10 present invention
12 user
14 plaster paste
16 trigger
18 bore
20 outlet nozzle
24 container
26 plaster powder
28 water bag
30 pressure ring
32 hand
34 plaster pump gun 36 nozzle end of bag
38 tip of nozzle
40 piston release handle
42 arrow
44 gun handle
46 piston plate
48 thin membrane
50 water chamber

DESCRIPTION OF THE PREFERRED EMBODIMENT(S)

In order that the invention may be more fully understood, it will now be described, by way of example, with reference to the accompanying drawings in which FIGS. 1 through 8 illustrate the present invention being a plaster ejector gun with disposable cartridge.

Figure 1:
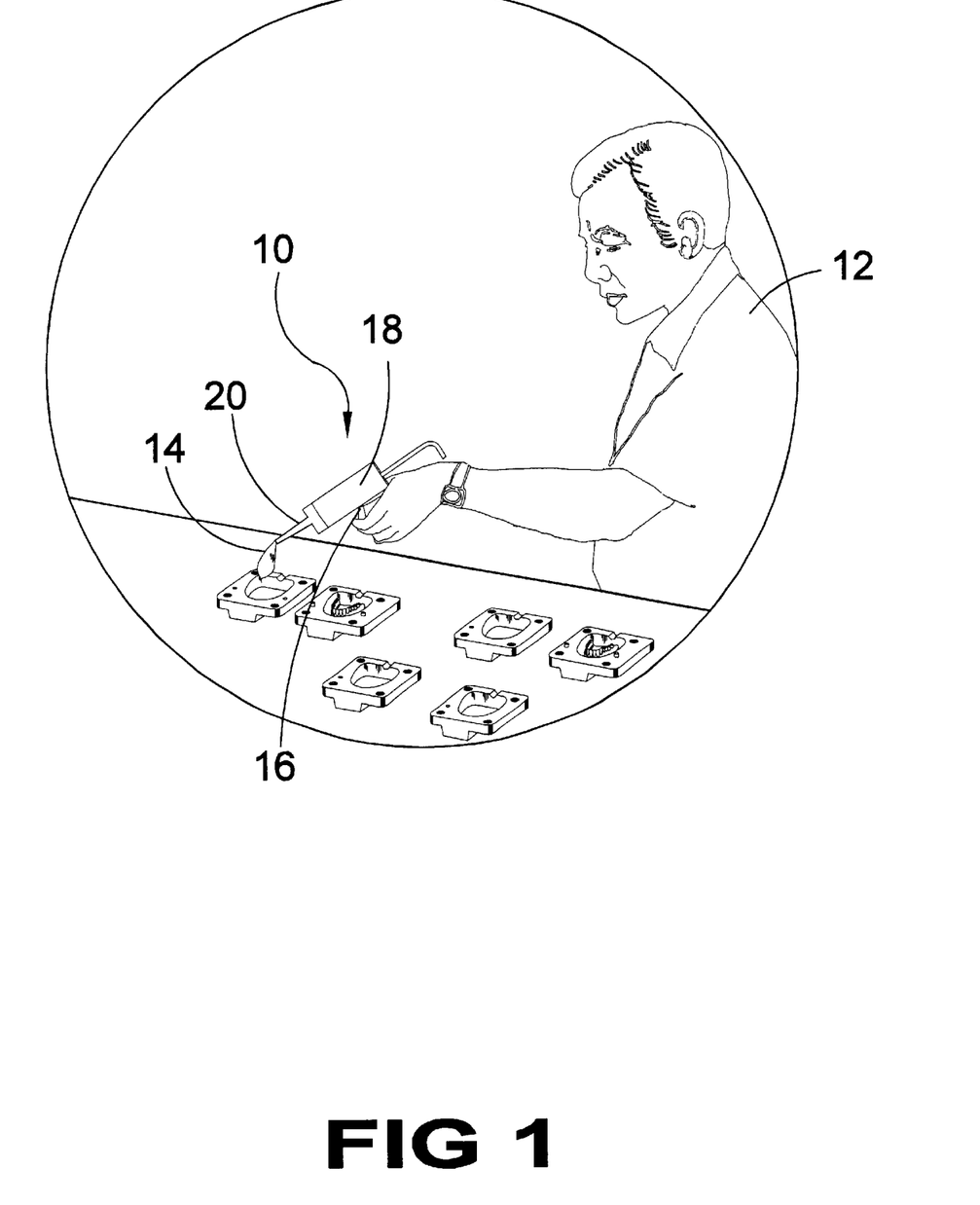
FIG. 1 is a pictorial illustration depicting the plaster pump of the present invention in use. Shown is a hand operated ejector gun having a disposable soft package of plaster paste (not shown) therein. The paste can be selectively dispensed by depressing the trigger which moves a piston in the through bore of the ejector gun toward the ejector gun nozzle.

Turning to FIG. 1, shown therein is a pictorial illustration depicting the plaster pump of the present invention 10 in use by a user 12. Shown is a hand operated ejector gun 10 having a disposable soft package of plaster paste (not shown) therein. The paste 14 can be selectively dispensed by depressing the trigger 16 which moves a piston in the through bore 18 of the ejector gun toward the ejector gun nozzle 20.

Figure 2:
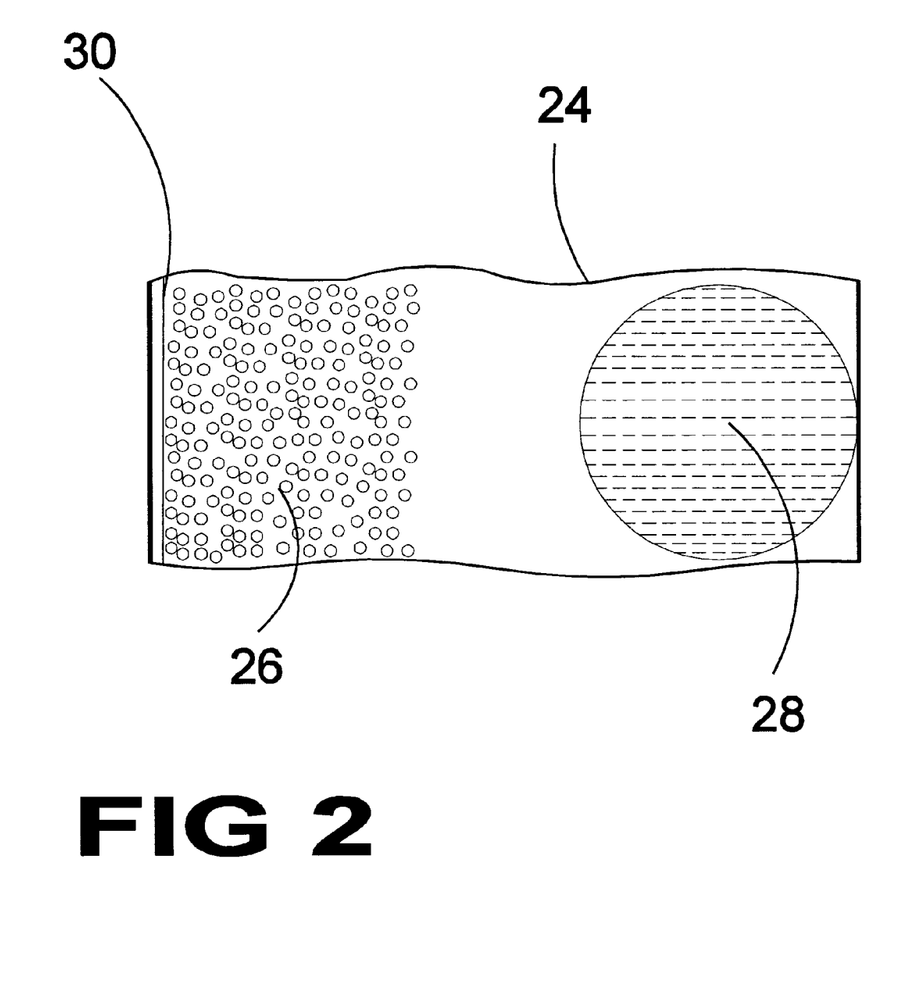
FIG. 2 is a view of the present invention depicting the disposable bag-like canister. Shown is a measured amount of dry plaster and a water chamber forming an integral part of said disposable bag-like canister.

Turning to FIG. 2, shown therein is a view of part of the present invention depicting the disposable plastic bag-like container or housing 24. Shown is a measured amount of dry plaster powder 26 and a separate water chamber or plastic sealed water bag 28 forming an integral part of said disposable bag-like container 24 being sealed by a pressure ring 30 at the nozzle end.

Figure 3:
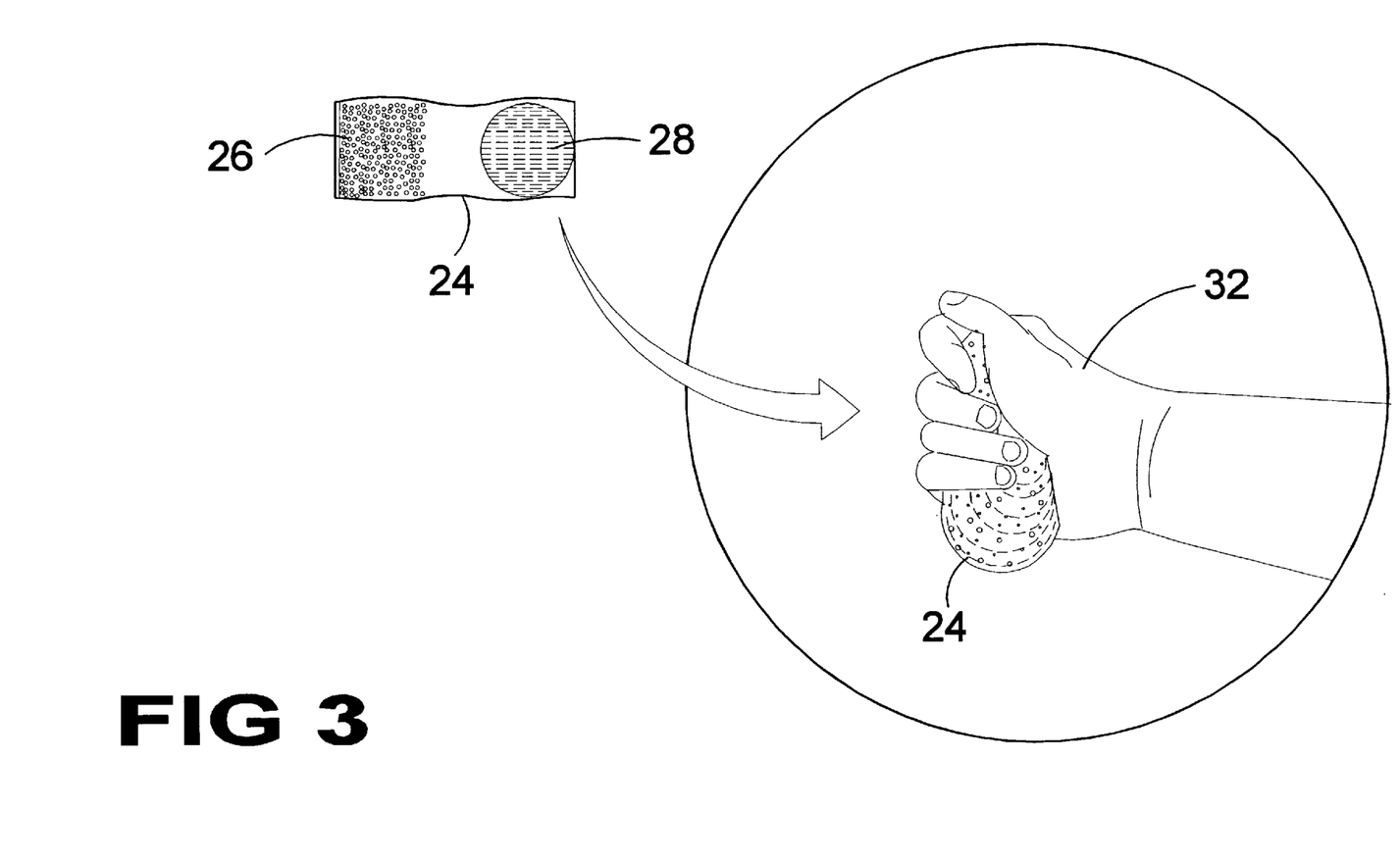
FIG. 3 is an illustration depicting a hand squeezing and kneading the bag-like cartridge.

Turning to FIG. 3, shown therein is an illustration depicting a hand 32 squeezing and kneading the bag-like cartridge 24. The plaster pump refill container 24 must be squeezed and kneaded so that the water bag 28 first mixes with the plaster powder 26. In operation the bag needs to be kneaded for about 30 seconds.

Figure 4:
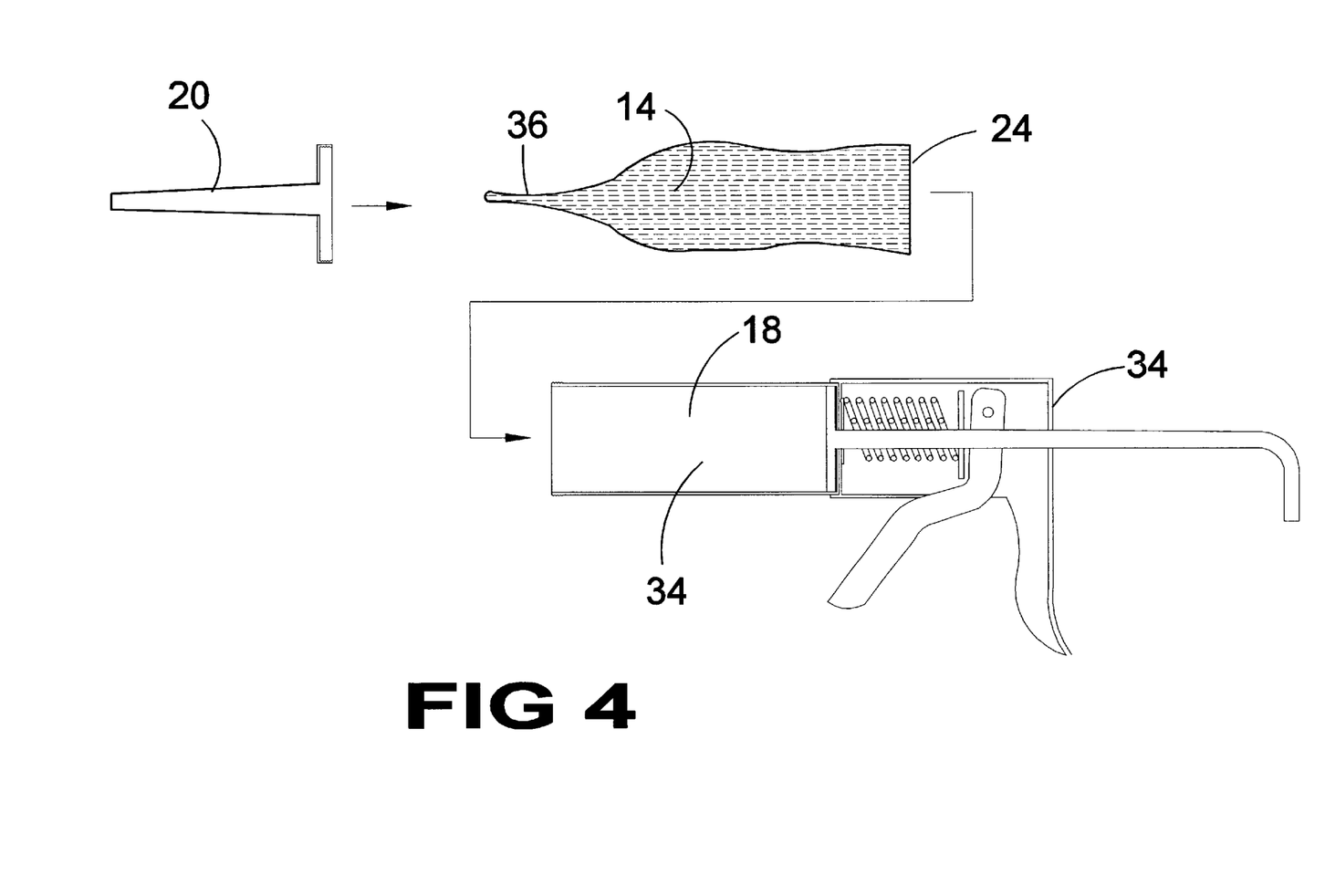
FIG. 4 is a view of the plaster pump and bag-like cartridge in an exploded view.

Turning to FIG. 4, shown therein is a view of the plaster pump gun 32 and bag-like cartridge 24 in an exploded view. After the plaster bag 24 is ready and mixed, the nozzle cap 20 is removed from the plaster pump gun 34 and the container 24 with mixed plaster paste 14 is inserted into the through bore 18 of the plaster gun 34. One distal end of container 24 is compressed and formed into a cylindrical nozzle-like end 36. The plaster paste container 24 is inserted into the ejector gun 34 by removing the ejector gun nozzle 20 and inserting a plaster container 24 therein. The soft nozzle 36 of the container 24 is positioned within the ejector gun nozzle 20 as the ejector gun nozzle 20 is attached to the ejector gun 34.

Figure 5:
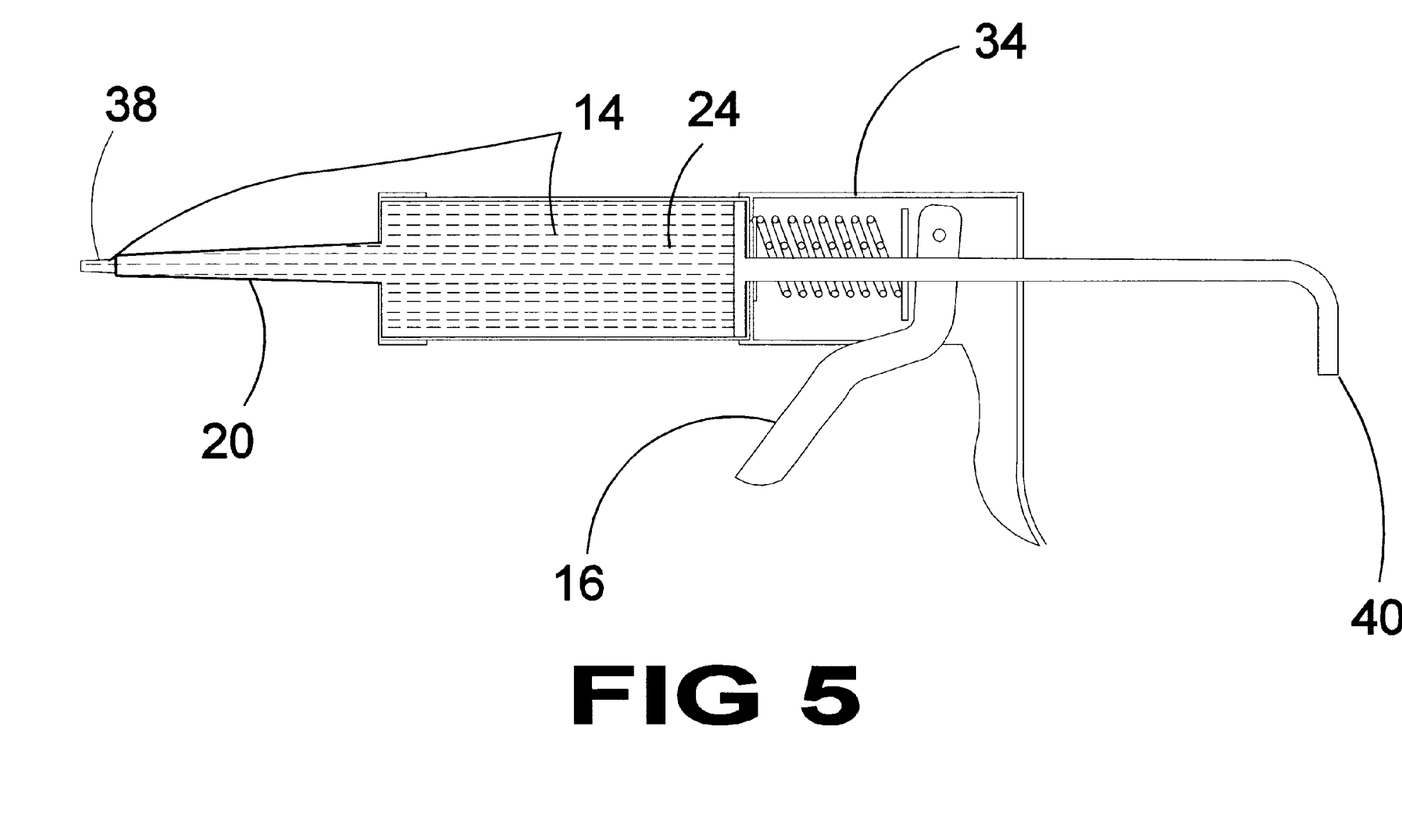
FIG. 5 is a view of the plaster pump having the bag-like plaster canister installed therein.

Turning to FIG. 5, shown therein is a view of the plaster pump gun 34 having the bag-like plaster container 24 installed therein. The plaster pump container 24 is loaded within the plaster pump 34 and wherein the container 24 remains sealed until the tip 38 of the container 24 is cut off. Also shown is the pump nozzle 20, the piston lever or trigger 16 and the piston release handle 40.

Figure 6:
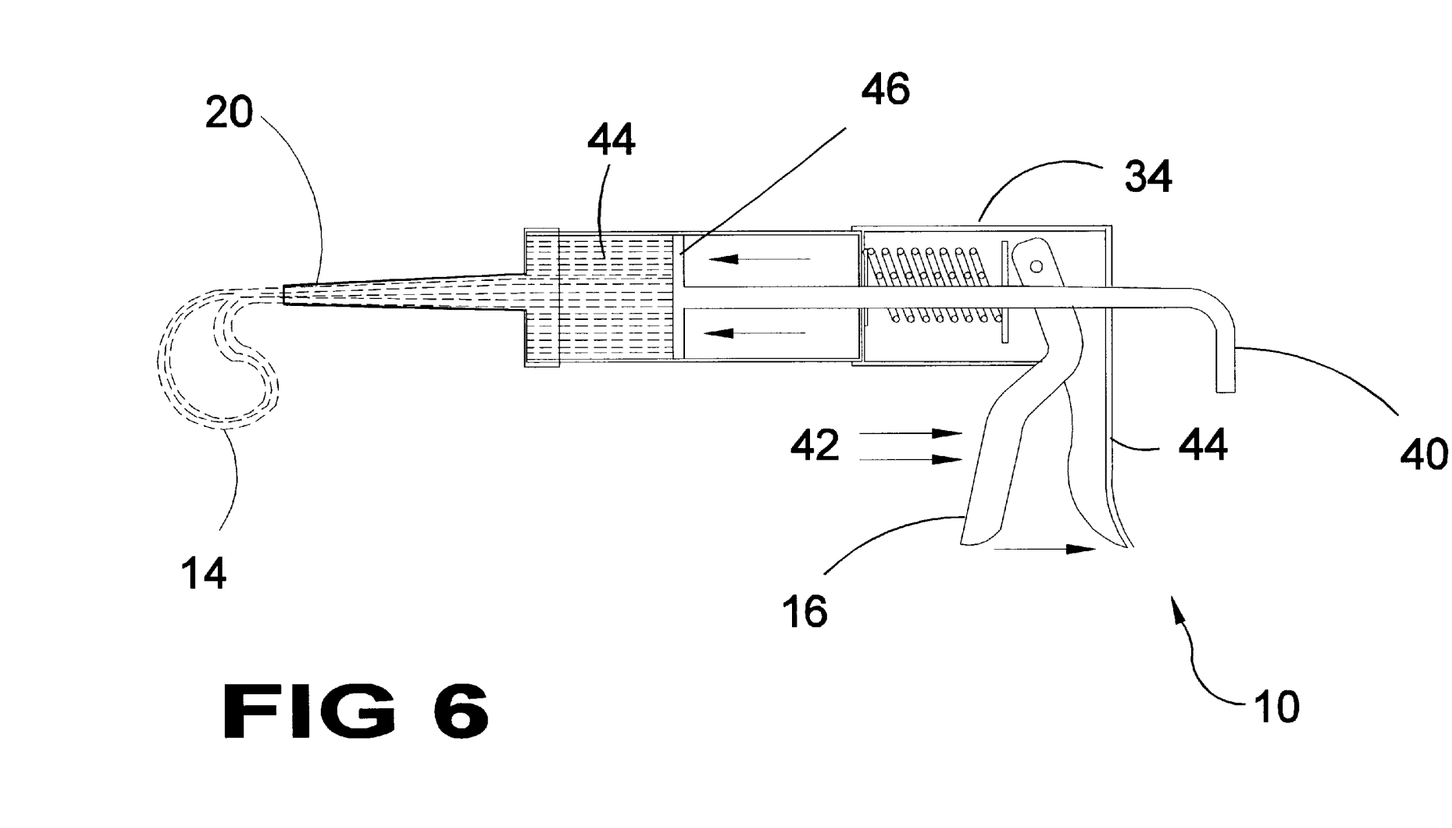
FIG. 6 is a sectional view of the present invention showing pressure being applied to the trigger of the ejector gun whereby plaster is dispensed.

Turning to FIG. 6, shown therein is a sectional view of the present invention 10 showing pressure being applied using arrows 42 to the trigger 16 of the ejector gun 34 whereby plaster mix 14 is dispensed. As pressure 42 is applied to the piston lever or trigger 16, the piston release plate 46 forces the plaster mix 14 to be expelled through the nozzle 20. As the ejector gun trigger 16 is depressed or squeezed toward gun handle 44 the ejector gun piston plate 46 compresses the plaster tube mixture container 24 and the ejector gun piston 46 increases the pressure until the soft plaster mix 14 is slightly extruded as a tip from the ejector gun nozzle 20. The extruded portion or tip of container 24 extending from ejector nozzle 20 is clipped or cut whereby the contents of the bag 24 can be expelled using the ejector gun trigger 16.

Figure 7:
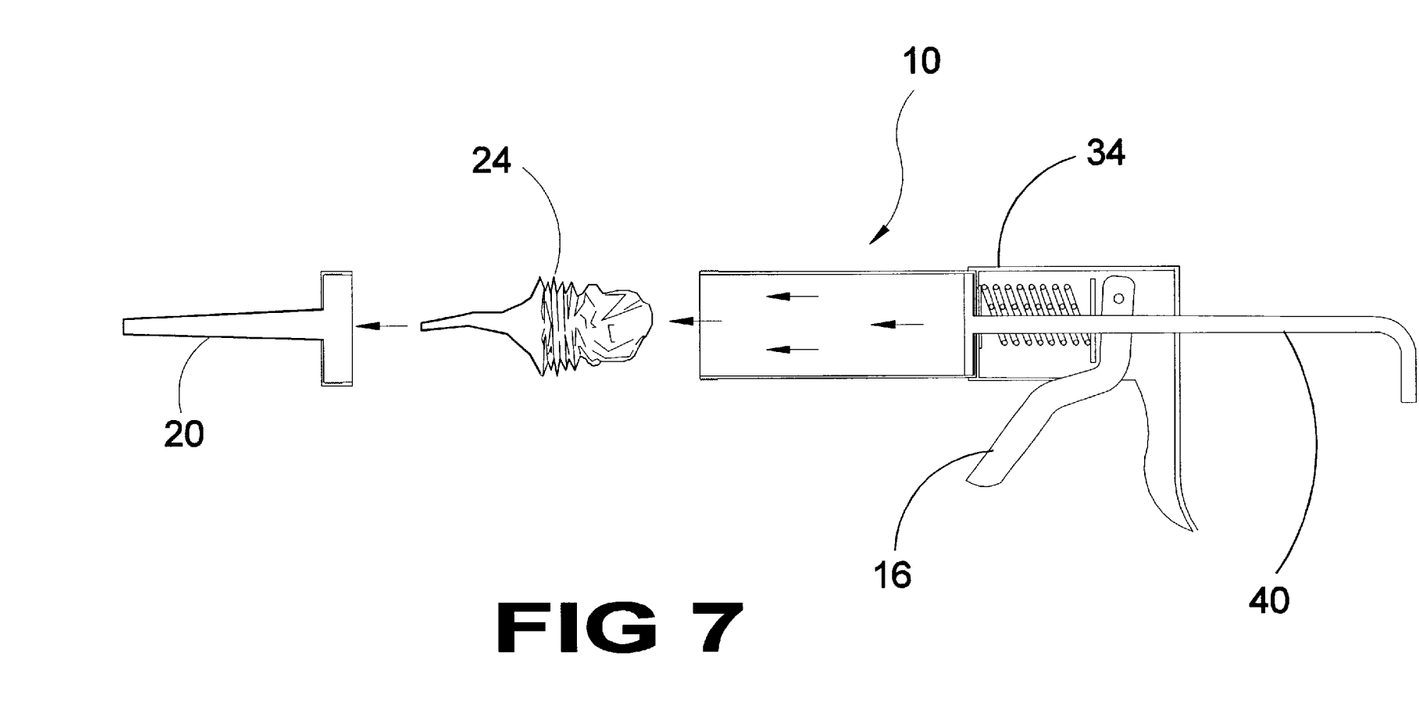
FIG. 7 is a view of the present invention showing the used bag-like canister removed from the ejector gun.

Turning to FIG. 7, shown therein is a view of the present invention 10 showing the used bag-like container 24 removed from the ejector gun 34. After the plaster container 24 is spent, the nozzle 20 is removed from the gun 34 housing and the spent bag 24 is removed therefrom. Thereby the waste contained in the plaster bag 24 is contained therein and no clean up is required. Because the soft package 24 covers all interior surfaces of the ejector gun 34, there is no clean up necessary for the sector gun.

Figure 8:
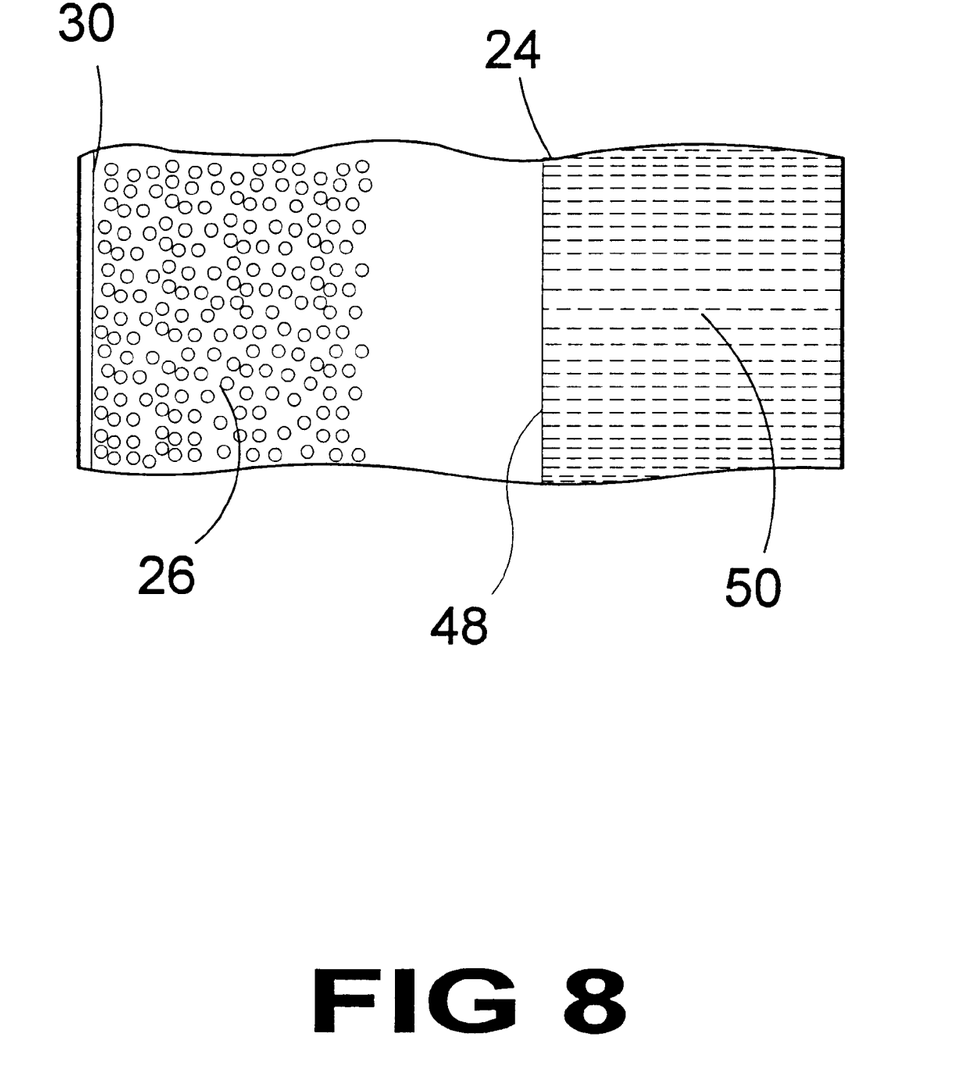
FIG. 8 is a view of the present invention depicting an alternative embodiment of the disposable bag-like container. Shown is a measured amount of dry plaster in a first chamber and a second water chamber separated by a membrane forming an integral part of said disposable bag-like canister.

Turning to FIG. 8, shown therein is a view of part of the present invention depicting an alternative embodiment of the disposable plastic bag-like container or housing 24. Shown is a measured amount of dry plaster powder 26 in a first chamber and a separate second water chamber 50 separated by a thin or weak seal or membrane 48 forming an integral part of said disposable bag-like container 24 being sealed by a pressure ring 30 at the nozzle end. The membrane 48 is ruptured by pressing on the water chamber 50 thereby allowing the water and plaster powder to mix.

I claim:

1. In an apparatus for extruding plaster from a plaster ejector gun, the gun having a through bore therein, an ejector nozzle having an outlet aperture therein, a piston for pressing and pushing plaster through the through bore, and a handle with movable trigger for operation of the piston by a user, the improvement comprising:

a) a flexible bag-like container,
   b) wherein said container is sealed having plaster powder disposed therein;
   c) said container having a second sealed bag of water disposed therein, said bag of water separated from said plaster powder by a portion;
   d) wherein said bag of water is burstable thereby having said plaster powder and said water form a mixture of plaster therein;
   e) said container being thereafter disposed in the through bore of the plaster ejector gun whereby the container can be pressed by the piston of the plaster ejector gun;
   f) an elongated tip formed in a first end of said container;
   g) said elongated tip of said container disposed in said ejector nozzle, said elongated tip having a hole therein; and,
   h) said hole allowing the extrusion of said mixture of plaster therethrough in response to pressure from the piston of the plaster ejector gun.

2. The apparatus of claim 1, wherein said bag-like container is made of plastic.

3. The apparatus of claim 1, further comprising a pressure ring disposed about the circumference of said container, said pressure ring disposed about said first end of said container.

4. The apparatus of claim 1, wherein said bag of water and said plaster powder is kneaded for about 30 seconds thereby forming a mixture of plaster.

5. A method of extruding plaster from a plaster ejector gun, the gun having through bore therein, an ejector nozzle having an outlet aperture therein, a piston for pressing and pushing plaster through the through bore and a handle with a movable trigger for operation of the piston by a user, comprising the steps of:

a) providing a first flexible bag-like container containing plaster powder;

b) forming a second sealed bag of water internal said first container;

c) sealing said first container having said plaster powder and said bag of water disposed therein;

d) bursting said bag of water thereby forming a mixture of plaster therein;

e) kneading said mixture of plaster;

f) forming an elongated tip in a first end of said first container;

g) placing said elongated tip internal the ejector nozzle of the plaster ejector gun;

h) placing said first container internal the through bore of the plaster ejector gun and placing the ejector nozzle onto the plaster ejector gun;

i) actuating the movable trigger of the plaster ejector gun thereby extruding a small tip of said first container through the ejector nozzle;

j) removing said small tip of said first container as it is extruded through the ejector nozzle; and, k) actuating the movable trigger of the plaster ejector gun to continue to extrude said mixture of plaster from the plaster ejector gun.

6. The method of claim 5, further comprising the step of kneading said mixture of plaster for about 30 seconds.

7. The method of claim 5, further comprising the step of forming said first flexible bag-like container from plastic.

8. The method of claim 5, further comprising the step of forming a pressure ring on said first end of said first container.

9. The method of claim 8, further comprising the step of forming said pressure ring about the circumference of said first end of said first container.

10. The method of claim 5, further comprising the step of covering all internal parts of the through bore of the plaster ejector gun with said first container whereby all parts of the plaster ejector gun remain clean.

11. The method of claim 10, further comprising the step of removing said first container from the ejector gun after usage of said first container.

12. In an apparatus for extruding plaster from a plaster ejector gun, the gun having a through bore therein, an ejector nozzle having an outlet aperture therein, a piston for pressing and pushing plaster through the through bore, and a handle with movable trigger for operation of the piston by a user, the improvement comprising:

a) a flexible bag-like container having a first and a second chamber disposed therein, said first and said second chambers separated by a membrane, said membrane being thin;

b) wherein said first chamber has plaster powder disposed therein;

c) wherein said second chamber has water disposed therein;

d) wherein said membrane of said container is burstable thereby having said plaster powder and said water form a mixture of plaster therein;

e) said container being thereafter disposed in the through bore of the plaster ejector gun whereby the container can be pressed by the piston of the plaster ejector gun;

f) an elongated tip formed in a first end of said container;

g) said elongated tip of said container disposed in said ejector nozzle, said elongated tip having a hole therein; and, h) said hole allowing the extrusion of said mixture of plaster therethrough in response to pressure from the piston of the plaster ejector gun.

13. The apparatus of claim 12, wherein said bag-like container is made of plastic.

14. The apparatus of claim 12, further comprising a pressure ring disposed about the circumference of said container, said pressure ring disposed about said first end of said container.

15. The apparatus of claim 12, wherein said bag of water and said plaster powder is kneaded for about 30 seconds thereby forming a mixture of plaster.

16. A method of extruding plaster from a plaster ejector gun, the gun having through bore therein, an ejector nozzle having an outlet aperture therein, a piston for pressing and pushing plaster through the through bore and a handle with a movable trigger for operation of the piston by a user, comprising the steps of:

a) providing a first flexible bag-like container having a first and a second chamber disposed therein, said first and second chambers separated by a thin membrane;

b) filling said first chamber with plaster powder;

c) filling said second chamber with water;

d) bursting said membrane of said container thereby forming a mixture of plaster therein;

e) kneading said mixture of plaster;

f) forming an elongated tip in a first end of said first container;

g) placing said elongated tip internal the ejector nozzle of the plaster ejector gun;

h) placing said first container internal the through bore of the plaster ejector gun and placing the ejector nozzle onto the plaster ejector gun;

i) actuating the movable trigger of the plaster ejector gun thereby extruding a small tip of said first container through the ejector nozzle;

j) removing said small tip of said first container as it is extruded through the ejector nozzle; and, k) actuating the movable trigger of the plaster ejector gun to continue to extrude said mixture of plaster from the plaster ejector gun.

17. The method of claim 16, further comprising the step of kneading said mixture of plaster for about 30 seconds.

18. The method of claim 16, further comprising the step of forming said first flexible bag-like container from plastic.

19. The method of claim 16, further comprising the step of forming a pressure ring on said first end of said first container.

20. The method of claim 19, further comprising the step of forming said pressure ring about the circumference of said first end of said first container.

21. The method of claim 16, further comprising the step of covering all internal parts of the through bore of the plaster ejector gun with said first container whereby all parts of the plaster ejector gun remain clean.

22. The method of claim 21, further comprising the step of removing said first container from the ejector gun after usage of said first container.

* * * * *